(12) United States Patent
Van Krieken

(10) Patent No.: US 7,867,736 B2
(45) Date of Patent: Jan. 11, 2011

(54) METHOD FOR PREPARING AN ORGANIC AMINE—LACTIC ACID COMPLEX

(75) Inventor: Jan Van Krieken, Gorinchem (NL)

(73) Assignee: Purac Biochem B.V., Gōrinchem (NL)

( * ) Notice: Subject to any disclaimer, the term of this patent is extended or adjusted under 35 U.S.C. 154(b) by 821 days.

(21) Appl. No.: 11/712,944

(22) Filed: Mar. 2, 2007

(65) Prior Publication Data

US 2007/0212765 A1  Sep. 13, 2007

Related U.S. Application Data

(60) Provisional application No. 60/780,070, filed on Mar. 8, 2006.

(30) Foreign Application Priority Data

Mar. 8, 2006  (EP) .................................. 06110854

(51) Int. Cl.
| | |
|---|---|
| *C12P 13/00* | (2006.01) |
| *C12P 7/56* | (2006.01) |
| *C07C 51/00* | (2006.01) |
| *C07C 51/42* | (2006.01) |
| *C07C 59/08* | (2006.01) |

(52) U.S. Cl. ....................... 435/128; 435/135; 435/146; 562/513; 562/514; 562/580; 562/589

(58) Field of Classification Search ........................ None
See application file for complete search history.

(56) References Cited

U.S. PATENT DOCUMENTS

| | | | | |
|---|---|---|---|---|
| 1,459,395 | A | | 6/1923 | Hamburger |
| 4,771,001 | A | * | 9/1988 | Bailey et al. ................. 435/139 |
| 6,509,179 | B1 | * | 1/2003 | Veldhuis-Stribos et al. . 435/139 |
| 6,667,417 | B2 | * | 12/2003 | Eyal et al. .................... 562/485 |
| 7,144,977 | B2 | * | 12/2006 | Eyal et al. .................... 528/354 |

FOREIGN PATENT DOCUMENTS

| | | |
|---|---|---|
| GB | 173479 | 11/1922 |
| WO | WO 00/17378 A2 | 3/2000 |
| WO | WO 02/074403 A1 | 9/2002 |
| WO | WO 02/090312 A1 | 11/2002 |
| WO | WO 2005/012364 A2 | 2/2005 |

OTHER PUBLICATIONS

Wasewar, Kailas L. et al., "Intensification of Conversion of Glucose to Lactic Acid: Equilibria and Kinetics for Back Extraction of Lactic Acid Using Trimethylamine," Chemical Engineering Science, vol. 59, No. 11, pp. 2315-2320, 2004.

Zbiobrowski, Jerzy et al., "Magnesium Carbonate As a Neutralizing Agent for the Lactic Acid Formed During Fermentation of Sugar Mashes," Przemysl Fermentacyjny, vol. 7, No. 1, pp. 3-6, 1964 (Abstract).

Kolomaznik, A. Blaha et al., "Manufacture of Magnesium Lactate," Chemical Abstracts, vol. 123, No. 317499f, 1995 (Abstract).

* cited by examiner

*Primary Examiner*—Herbert J. Lilling
(74) *Attorney, Agent, or Firm*—Oliff & Berridge, PLC

(57) ABSTRACT

The invention relates to a method for preparing a complex of an organic amine and lactic acid in a reactor, characterized in that a water-miscible organic amine is brought into contact with magnesium lactate in an aqueous medium in the reactor to form the complex and precipitated magnesium hydroxide, after which the magnesium hydroxide is separated from the complex.

11 Claims, 1 Drawing Sheet

Scheme
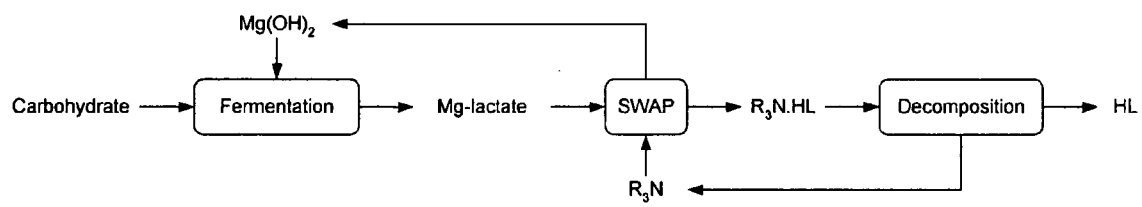

METHOD FOR PREPARING AN ORGANIC AMINE—LACTIC ACID COMPLEX

This nonprovisional application claims the benefit of U.S. Provisional Application No. 60/780,070, filed Mar. 8, 2006.

The present invention relates to a method for preparing a complex of an organic amine and lactic acid in a reactor.

Lactic acid is a hydroxy acid used primarily in the food industry. It is also used in the polymer industry for the preparation of polylactic acid, which is a biodegradable polymer.

Most of the commercial processes for the preparation of lactic acid are based on the fermentation of carbohydrates by microorganisms. These processes require strict control of temperature and pH. A common feature to all the fermentation processes is the need to neutralize the acids excreted by the microorganisms in the process. A drop in pH below a critical value, depending on the micro-organism used in the process, could damage the micro-organism's metabolic process and bring the fermentation process to a stop. Therefore, it is common practice to add $Ca(OH)_2$ to the fermentation reaction and thus produce calcium lactate. The use of sulfuric acid to liberate lactic acid from calcium lactate subsequently generates calcium sulfate as solid waste, which is currently disposed as gypsum. An increase in the production of lactic acid will generate a substantial increase in solid waste, which could eventually become an unbearable burden to the environment. In addition to this, and in spite of the various separation schemes developed for fermentation processes, the preparation of lactic acid of high purity still remains an elusive goal. If the desired product is a specific lactate salt, with conventional processes a calcium lactate salt resulting from the fermentation with calcium base as a neutralizing agent is prepared first. Then the calcium lactate is converted into lactic acid by means of sulfuric acid addition under formation of gypsum, and subsequently the lactic acid is converted into the lactate salt desired. It goes without saying that this process for preparing lactate salt is laborious, time-consuming, and results in unwanted solid waste in the form of gypsum.

A process for the preparation of lactic acid without the formation of gypsum is known from EP 614983. Herein ammonia is used as neutralizing agent and thus ammonium lactate is formed. Such a process efficiently prevents the formation of gypsum, but has the disadvantage that the formed ammonium lactate is difficult to thermally cleave to obtain the desired lactic acid, and for that reason is converted into an ester with butanol, after which the ester is converted to lactic acid.

It is a purpose of the present invention to provide an improved process for the production of lactic acid and/or lactate salt, without forming gypsum and obtaining products that can easily be converted to lactic acid.

It is a further purpose of the invention to provide an environmentally friendly process without forming large quantities of solid waste for the preparation of lactic acid and/or lactate salt.

It is another purpose of the invention to provide a process for the preparation of lactic acid and/or lactate salt, comprising a cleavage step.

Other objects of the invention will become apparent as the description proceeds.

According to the present invention lactic acid and/or lactate salt is prepared via an improved process comprising that a water-miscible organic amine having a pKa>9 is brought in a reactor into contact with magnesium lactate in an aqueous medium to form an organic amine-lactic acid complex and magnesium hydroxide, after which the precipitated magnesium hydroxide is separated from the complex. This process may be conducted virtually free of any solid or liquid waste effluents other than water, hence being environmentally friendly. The present invention provides a process for the preparation of lactic acid and/or lactate salt from a medium comprising magnesium lactate. The use of magnesium lactate rather than calcium lactate has a further advantage in that it allows a more easy separation of the crystals from the supernatant, e.g. a fermentation broth. In the prior art several publications describe the possibility of using a magnesium base as neutralizing agent in lactic acid fermentations and/or (further) processing to lactic acid Magnesium carbonate as a neutralizing agent for the lactic acid formed during fermentation of sugar mashes, Zbiobrowsky, Jerzy; Lesniak Wladyslaw, Przemysl refment, (1964), 7(1), 3-6 describe the use of magnesium carbonate as neutralizing agent for lactic acid produced in fermentation of molasses and white sugar. The magnesium lactate is converted into magnesium carbonate and sodium lactate over an ion exchange column. The use of an ion exchange column, however, has the disadvantage that it needs an additional step of regeneration after its use.

Also JP-B4-63000038 is directed to the lactic acid recovery from a fermentation by converting the acid into its magnesium salt and evaporation at a temperature above 50° C. This resulted in crystalline magnesium lactate, which was converted into lactic acid using sulfuric acid, after which the magnesium sulfate formed was removed with an ion-exchange resin.

Manufacture of magnesium lactate, Kolomaznik, A. Blaha, S. Saha, L. Saha, Czech Rep. CZ 279, 449, 12 Apr. 1995 is directed to the production of magnesium lactate by fermentation of wey (lactose) and neutralization with magnesium oxide, hydroxide, or carbonate. The conversion, at pH 4.5-5.0 was significantly higher than in the presence of conventional Ca-bases.

In U.S. Pat. No. 1,459,395 the purification of lactic acid by neutralization of commercial (dark) lactic acid with magnesium oxide, hydroxide or carbonate to produce magnesium lactate was described. The magnesium lactate is acidulated with concentrated sulfuric acid in a suitable solvent. After removing the magnesium sulfate by filtration the resulting solution is distilled to remove solvent. The pure lactic acid remains as a residue. Also a conversion from calcium lactate to magnesium lactate with the formation of calcium sulfate (a so-called SWAP reaction, i.e. conversion from one salt to another) is mentioned.

GB 173,479 describes a process for the purification of lactic acid from fermentation in which the lactic acid in solution is converted into magnesium lactate. The lactic acid in solution may be converted into a more soluble lactate salt such as calcium lactate prior to its conversion to magnesium lactate. The resulting magnesium lactate solution is acidified with sulfuric acid and the lactic acid is recovered by extraction with, for instance, acetone. By suspending the magnesium salt solution in acetone and then acidifying to form precipitated magnesium sulfate and lactic acid, the extraction and acidulation steps may also be combined.

These prior art processes provide gypsum or another salt as byproduct, which should be separated and removed and therefore adds to the process costs.

WO 00/17378 is directed to the fermentation of sugar to form lactic acid. The pH of the fermentation is adjusted to 5.5 to 6.5 by addition of calcium or magnesium hydroxide. The magnesium lactate is converted with hydrochloric acid to form lactic acid and magnesium chloride. The lactic acid is extracted by LLE (liquid-liquid extraction) with isoamyl alcohol, an amine, or ether. The magnesium chloride is decomposed thermally to hydrochloric acid and magnesium oxide. Although the process does not produce a salt as byproduct, the need of high decomposition temperatures (above 500° C.) in the presence of corrosive hydrochloric acid, requiring special inert equipment, is a certain disadvantage of this method, whereas a complicated extraction step further adds to the disadvantages of this method.

In WO 2005/12364 the conversion of magnesium lactate was described to other lactate salts by using strong inorganic bases.

Recovery of lactic acid from ammonium lactate or alkylammonium lactates has also been disclosed, for instance in WO 02/074403 wherein a method for the recovery of an organic acid, such as a heat stable lactic acid, is described from a feed stream comprising at least one of an organic acid amide, an organic acid ammonium salt or an alkylamine-organic acid complex. The alkylamine typically is a water immiscible higher alkylamine such as lauryl amine. Recovery therefore requires that the feed stream is mixed with an azeotroping agent and the mixture is fed to a fractional distillation apparatus or reactor. The azeotroping agent is a hydrocarbon capable of forming at least one azeotrope with the organic acid that is produced by the thermal decomposition of the amide, ammonium salt, or complex in the feed stream. The vapor stream is condensed in condenser to a liquid stream, and the organic acid is recovered in the liquid stream that is produced. This method needs the use of a relatively complicated azeotropic distillation step.

According to the present invention the magnesium lactate is preferably obtained by fermentation of a carbohydrate at pH 5-7 by at least one of magnesium hydroxide, magnesium oxide, and magnesium carbonate.

In another embodiment magnesium lactate is allowed to crystallize and precipitate from the fermentation broth (optionally after separation of the biomass) and subsequently separated. To initiate crystallization, the fermentation broth may optionally be concentrated. The crystallization-precipitation-separation step additionally purifies the magnesium lactate from contaminants.

The whole process is clearly directed to the use of magnesium base as a neutralizing agent, which keeps the fermentation broth at a pH level that is not harmful to the microorganism, which is in many cases a pH of about 5 to 7.

Although the use of a magnesium base as neutralizing agent in lactic acid fermentations is known, it has never been acknowledged that the use of a water-miscible organic amine and magnesium lactate has advantages over common processes using compounds such as calcium or sodium lactate and other lactate salts formed when using other neutralizing agents. Nor are these advantageous properties utilized for developing an environmental-friendly solid waste-free process with improved purification and separation of lactic acid and/or lactate. Further, none of the publications mentioned above teach the reaction conditions necessary for such a process.

To this end, the present invention is directed to a process for the preparation of lactic acid and/or lactate by bringing a water-miscible organic amine in a reactor in contact with magnesium lactate in an aqueous medium to form a complex and precipitated magnesium hydroxide, after which the magnesium hydroxide is separated from the complex medium comprising organic amine lactate complex, where after the organic amine lactate is separated and further treated to give lactic acid and the organic amine, for instance by a thermal treatment. The lactic acid obtained may be converted into a lactate salt by any conventional method known in the art.

With the process according to the invention an organic amine lactate salt (complex) is formed (in liquid form or in solution) and magnesium hydroxide is precipitated, which precipitate can be recycled to the first step for neutralizing the fermentation.

The term "water-miscible" means that the organic amine should be at least very miscible with water, which means a water solubility better than 250 vol/vol, preferably better than 400 vol/vol, most preferably having unlimited solubility.

Preferred amines according to this invention have pKa>9, more preferably pKa>9.5, such as trimethylamine and triethylamine because it ensures proper conversion, which amines are particularly preferred. Most preferably, the pKa is at least 10. The aqueous medium is most preferably water.

The organic amine complex obtained should be cleavable to obtain lactic acid. Therefore the complex is cleaved into lactic acid and the water-miscible organic amine, wherein the recovered water-miscible organic amine may be recycled to the reactor and be used again. This method prevents waste and unnecessary loss of valuable compounds. This cleavage reaction is preferably performed by a heat treatment, but any other method such as electro-dialysis or esterification may also be used.

The thermal decomposition of the lower trialkylammonium lactate (such as trimethyl- and triethylammonium lactate) can be performed according to the method of Wasewar et al., Chemical Engineering Science (2004), 59(11), 2315-2320. The thermal decomposition of these lower trialkylammonium lactates is substantially easier than the decomposition of ammonium lactate, as exemplified in, for instance, WO 02/090312.

It should be noted that the direct manufacture of complexes of alkylamine with lactic acid is known from other inorganic lactates. For instance, U.S. Pat. No. 5,510,526 describes the use of sodium lactate for making trialkylamine complex. The trialkylamines used are contrary to the present invention typically water immiscible higher trialkylamines. This method has various disadvantages such as the need to work under $CO_2$ pressure, which is rather unsafe and therefore needs special equipment, whereas the alkylamines are considerably more expensive than the simple water-miscible amines presently used, such as triethylamine.

The process according to the invention is preferably carried out continuously, using the previously mentioned recycle steps.

In a preferred embodiment according to the invention, the magnesium lactate is obtained by fermentation of a carbohydrate at pH 5-7 by at least one of magnesium hydroxide, magnesium oxide, and magnesium carbonate. It is specifically preferred that the precipitated and separated magnesium hydroxide is recycled to the fermentation step.

In another preferred embodiment according to the invention, the complex is cleaved into lactic acid and the water-miscible organic amine, preferably by heating. The water-miscible organic amine as obtained after cleavage of the complex may be recycled to the SWAP-reactor (the reactor wherein the SWAP reaction is performed).

In another even more preferred embodiment according to the invention, the reaction is therefore carried out by obtaining the magnesium lactate by fermentation of a carbohydrate wherein the pH is brought to 5-7 by at least one of magnesium hydroxide, magnesium oxide, and magnesium carbonate and cleaving the complex into lactic acid and the water-miscible organic amine, recycling the precipitated and separated magnesium hydroxide to the fermentation step and recycling the water-miscible organic amine to the SWAP-reactor.

As mentioned above, the magnesium hydroxide and the lactate salt formed can be easily separated from each other. The magnesium hydroxide particles can be separated by filtration or sedimentation. Preferably, the magnesium hydroxide formed is directly separated from the reaction medium, because at that point in time the particle size and structure of the magnesium hydroxide particles are optimal. Optionally, the magnesium hydroxide particles are washed with water after separation. In the case of a continuous process the magnesium hydroxide particles are preferably continuously removed from the reaction medium and recycled. In the case of a batch process it is preferred that the magnesium hydroxide particles are removed from the reaction medium directly after formation or as soon as technically possible.

BRIEF DESCRIPTION OF THE FIGURE

The present invention is further illustrated by the Scheme and the following Example. In the Scheme a block diagram is shown of a process according to the invention.

The Example merely serves for illustration and should not be construed as being limitative. In the Scheme $R_3N$ stands for the water-miscible amine and HL stands for lactic acid.

The Scheme shows a preferred process wherein a carbohydrate is brought to a fermentor for fermenting the carbohydrate to magnesium lactate. The magnesium lactate is subjected to a SWAP reaction in a reactor, into which a trialkylamine is introduced and magnesium hydroxide is expelled and recycled to the fermentor to act as a neutralizing agent. The organic amine complex that is formed in the reactor is then cleaved (decomposed) to give lactic acid and trialkylamine. The trialkylamine is recycled to the reactor.

The following is a specific example of the process according to the invention.

A 250 mL Erlenmeyer flask was charged with 5.0 g (21 mmole) of magnesium lactate dihydrate crystals (obtained by Purac Biochem B.V. by a common commercial process) and 95 mL of demineralized water. The mixture was heated to about 30° C. by means of a microwave oven to facilitate the dissolution of the magnesium lactate crystals. To the clear solution 4.1 g (40.5 mmole) of triethylamine were added portion wise (in about 1 g portions) under stirring with a magnetic stirrer bar. The final pH was about 10.5. The mixture was stirred for another hour at room temperature and the magnesium hydroxide was filtered off by means of vacuum, using a paper filter to obtain a clear supernatant solution. The resulting solution contained 1070 ppm of $Mg^{2+}$ ions, indicating about 80% conversion of magnesium lactate.

The invention claimed is:

1. A method for preparing a complex of an organic amine and lactic acid in a reactor, characterized in that a water-miscible organic amine is brought into contact with magnesium lactate in an aqueous medium in the reactor to form the complex and precipitated magnesium hydroxide, after which the magnesium hydroxide is separated from the complex.

2. The method according to claim 1 wherein the amine has a pKa>9.

3. The method according to claim 1 wherein the amine is a trialkylamine.

4. The method according to claim 3 wherein the amine is at least one of trimethylamine and triethylamine.

5. The method according to claim 1 wherein the aqueous medium is water.

6. The method according to claim 1 wherein the magnesium lactate is obtained by fermenting a carbohydrate by neutralizing with at least one of magnesium hydroxide, magnesium oxide, and magnesium carbonate.

7. The method according to claim 6 wherein the separated magnesium hydroxide is recycled to the fermentation.

8. A method for preparing and cleaving a complex of an organic amine and lactic acid in a reactor, characterized in that a water-miscible organic amine is brought into contact with magnesium lactate in an aqueous medium in the reactor to form the complex and precipitated magnesium hydroxide, after which the magnesium hydroxide is separated from the complex and the complex is cleaved into lactic acid and the water-miscible organic amine.

9. The method according to claim 8 wherein the complex is cleaved by heating.

10. The method according to claim 8 wherein the water-miscible organic amine as obtained after cleavage of the complex is recycled to the reactor.

11. The method according to claim 1, wherein the amine has a pKa>10.

* * * * *